(12) United States Patent
Skiffington et al.

(10) Patent No.: US 9,568,413 B1
(45) Date of Patent: Feb. 14, 2017

(54) LUMINOMETER AND CHAMBER

(71) Applicant: Charm Sciences, Inc., Lawrence, MA (US)

(72) Inventors: Richard Skiffington, North Reading, MA (US); Mark Page, Nashua, NH (US)

(73) Assignee: Charm Sciences, Inc., Lawrence, MA (US)

( * ) Notice: Subject to any disclaimer, the term of this patent is extended or adjusted under 35 U.S.C. 154(b) by 198 days.

(21) Appl. No.: 14/600,514

(22) Filed: Jan. 20, 2015

Related U.S. Application Data

(60) Provisional application No. 61/929,669, filed on Jan. 21, 2014.

(51) Int. Cl.
*G01N 21/94* (2006.01)
*G01N 21/03* (2006.01)
*G01N 21/59* (2006.01)
*G01N 21/62* (2006.01)

(52) U.S. Cl.
CPC ............. *G01N 21/03* (2013.01); *G01N 21/59* (2013.01); *G01N 21/62* (2013.01); *G01N 2201/0221* (2013.01)

(58) Field of Classification Search
CPC ........ G01N 21/03; G01N 21/59; G01N 21/62; G01N 2201/0221
USPC ............... 250/221, 222.2, 207, 239; 422/404
See application file for complete search history.

(56) References Cited

U.S. PATENT DOCUMENTS

| | | | | |
|---|---|---|---|---|
| 4,213,703 | A * | 7/1980 | Haunold | G01N 21/0332 250/361 C |
| D393,601 | S * | 4/1998 | Skiffington | D10/78 |
| 5,917,592 | A * | 6/1999 | Skiffington | G01N 21/76 356/244 |
| 6,055,050 | A * | 4/2000 | Skiffington | G01N 21/76 356/244 |
| 6,653,147 | B2 * | 11/2003 | DiCesare | B01L 3/5029 435/5 |
| 7,030,403 | B2 * | 4/2006 | Feldsine | G01N 21/76 250/239 |
| 7,544,961 | B2 * | 6/2009 | Feldsine | G01N 21/76 250/239 |

* cited by examiner

*Primary Examiner* — Seung C Sohn
(74) *Attorney, Agent, or Firm* — MacCord Mason PLLC

(57) ABSTRACT

An improved luminometer, chamber insert, and deactivator is shown and described. In one embodiment, the device comprises a luminometer for use with a test sample holder and is configured to determine the emitted light from the test sample holder. Typically, the luminometer includes a housing having a sample port, a photomultiplier assembly, and a chamber having a mirrored inner side face. In certain examples, an improved chamber for a luminometer comprises an insert portion, a photomultiplier portion, and a deactivator.

20 Claims, 16 Drawing Sheets

LUMINOMETER AND CHAMBER

This application claims the benefit of provisional application No. 61/929,669, filed Jan. 21, 2014.

FIELD OF THE TECHNOLOGY

The present disclosure relates generally to analytical testing, and more particularly to improved luminometer and luminometer chambers.

BACKGROUND

Determination of cleanliness in industrial, health care and other settings is important for maintaining good hygiene and sanitation. For example, the surfaces of equipment used for food handling, storage or processing are major sources of microbial and allergen contamination. Microbial contamination can lead to decreased shelf life of products and, if pathogens are present, transmission of disease. Similarly, unexpected allergens on food contact surfaces may contaminate food. Such contamination has the potential to cause adverse reactions, such as an allergic reaction including hives, anaphylaxis and death, in sensitive people who consume or otherwise contact the contaminated food.

Microbial culturing can be used to determine the presence of microorganisms. Culturing, however, is time consuming and, therefore, the necessary "real time" feedback to sanitation and food preparation personnel may not be available. As a result, food exposed to surfaces that are later found to contain potentially harmful microorganisms could enter the food supply. Therefore, hygiene and sanitation analysis of a wide variety of materials in industrial, health care and other settings often depend upon the measurement of an intensity of light beam.

Therefore, luminometers, photometers and other instruments for detecting and measuring absorption or emission of light from a test sample can be useful measures of chemical and biological systems and changes, particularly in the determination of emitted light from test samples containing luminescent components. Luminometers, photometers and the like often measure light emission, wherein the test sample, whose light is to be determined, can be maintained at an acceptable optical temperature or other required conditions. Photometer analyzers are typically included for use with multiple bioluminescent or chemiluminescent assay tests. In some applications, a portable analyzer works in conjunction with a varying number of sample holders to determine and measure the presence of ATP, pesticides, phosphatase, and somatic cells; predict shelf life; and also to conduct general microbial quality tests for a wide variety of products. Typically, these devices are capable of storing and sorting assay data in its memory, and transferring information to a display panel or printer or a computer system.

Traditional devices may include a sample chamber with an entrance port, into which a test vial containing the test sample to be determined is inserted. In particular examples, the test vial containing the sample employed in the test sample holder is a transparent or translucent vial, which permits the passage or emission of the emitted exposed light, for example, in a bioluminescent assay, and, for example, permits light transmission of from about 300 to 650 nanometers, which is visible light range. The test vial with the test sample therein may be separately inserted, or may be removed as a detachable component of a separate test sample holder device, such as an elongated tube, for example, a POCKETSWAB device, (a registered trademark of Charm Sciences, Inc., of Lawrence, Mass.), or other test sample holders described herein.

However, conventional luminomter systems and devices require efficient use of photomultiplier tubes, photodiodes or the like for the sensitivity needed to properly detect light levels to ensure product quality and safety.

Therefore, Applicants desire systems and methods for improved luminomter efficiency of photon counting, without the drawbacks presented by the traditional systems and methods.

SUMMARY

In accordance with the present disclosure, a luminometer is provided for analytical testing. This disclosure provides an improved luminometer chamber that is convenient, efficient, and safe for the user, particularly when used for detecting and measuring absorption or emission of light from a test sample to measure chemical and/or biological systems and changes.

One embodiment of the present disclosure is a luminometer for use with a test sample holder to determine emitted light from the test sample holder. The luminometer includes a housing, a photomultiplier assembly, and a chamber having a mirrored inner side face. The housing typically includes a sample port and an entrance tube aligned with the sample port and accept the test sample holder into the housing. The photomultiplier assembly typically has at least one photomultiplier tube. The chamber is typically positioned between the entrance tube and in an optical path with the photomultiplier tube.

In some examples, the entrance port is light blocking. The photomultiplier assembly may include a pair of photomultiplier tubes. The photomultiplier assembly may include a receptor panel. The receptor panel may include a photomultiplier receiver. The absorbing window inner side face may include a layer of black paint.

Another embodiment of the present disclosure is a luminometer having a housing with an entrance to accept a test sample, and including an insert portion having a mirrored inner face, a photomultiplier portion, and a deactivator. The insert portion is typically positioned within the cavity with a first opening aligned with the entrance and a second deactivator opening. The photomultiplier portion is configured to support at least one photomultiplier tube. Further, the deactivator is typically secured in the second deactivator opening.

In some examples, the chamber includes an upper chamber attachment block. The chamber block may include a tube cavity receiving an entrance tube. The chamber block may include a front assembly lip aligning with the housing. The insert may include a front tube opening. The insert may include a rear deactivator opening. Further, the insert may include a top opening. In addition, the insert portion may include a deactivator cavity to receive the pressed deactivator. The insert portion may include a brace support.

In some examples, the photomultiplier portion includes a receptor cavity that is configured to receive a photomultiplier receptor. Further, the assembly may include a photomultiplier receptor.

Yet another embodiment of the present disclosure is a luminometer having a housing, a photomultiplier assembly, and a chamber with a mirrored inner side face. The luminometer generally is for use with a test sample holder to determine the emitted light from the test sample holder. The housing typically includes a sample port and an entrance tube that is generally aligned with the sample port to accept the test sample holder into the housing. The photomultiplier assembly typically includes at least one photomultiplier tube. The chamber is typically positioned between the entrance tube and the photomultiplier tube. Further, the chamber may include first tube opening to receive the entrance tube and a second deactivator opening. In addition, a deactivator may be secured in the second deactivator opening.

In some examples, the device includes an absorbing window inner side face. In particular examples, the absorbing window inner side face includes a layer of black paint.

A further embodiment of the present disclosure is to provide an improved chamber in a luminometer having a housing with an entrance to accept a test sample. The chamber may include an insert portion, a photomultiplier portion and a pressed polytetrafluoroethylene (PTFE) deactivator or a mirrored surface. Typically, the insert portion is chosen from a polytetrafluoroethylene (PTFE) pressed insert or a mirrored surface, and is generally positioned within the cavity and has a first opening that is generally aligned with the entrance and a second deactivator opening. The photomultiplier portion includes at least one photomultiplier tube. Further, the pressed deactivator is typically secured in the second deactivator opening.

In some examples, the chamber includes an upper chamber attachment block. The chamber block may have a tube cavity that is generally adapted to receive an entrance tube. The chamber block may have at least one fastener hole. Further, the chamber block may have a front assembly lip that is generally adapted to align with the housing.

In other examples, the pressed insert includes a front tube opening. Further, the pressed insert may have a rear deactivator opening. In addition, the pressed may have a top opening. In particular examples, the pressed insert includes outer walls having a thickness of about one millimeter to about ten millimeters. Further, the outer walls may have attachment points.

The insert portion may have a deactivator cavity that is generally adapted to receive the pressed deactivator. Further, the insert portion may have a brace support. The insert portion may have fastener holes. In other examples, the photomultiplier portion may have a rear assembly lip. Further, the rear assembly lip may include fastener holes. In particular examples, the photomultiplier portion may have a receptor cavity that is adapted to receive a photomultiplier receptor. The photomultiplier portion may include a photomultiplier receptor. The photomultiplier portion may include at least one adjustment slit. The photomultiplier portion may include plurality of fastener apertures. In yet further examples, the pressed deactivator is about one millimeter to about ten millimeters in thickness.

A further embodiment of the disclosure is a luminometer for use with a test sample holder to determine the emitted light from the test sample holder. The luminometer may comprise a housing, a photomultiplier assembly and a chamber. Typically, the housing may have a sample port and an entrance tube that is generally aligned with the sample port and is adapted to accept the test sample holder into the housing. The photomultiplier assembly is typically within the housing and has at least one photomultiplier tube. The chamber is typically positioned between the entrance tube and in an optical path with the photomultiplier tube and has a PTFE pressed insert or a mirrored surface.

In some examples, the housing is portable. For instance, the housing may have a battery casing. Further, the housing may be handheld. For example, the handheld housing may have opposing grips. In addition, the housing may have a touch screen display. The entrance port may be light blocking.

In other examples, the photomultiplier assembly may include a pair of photomultiplier tubes. The photomultiplier assembly may have a receptor panel. The receptor panel may have a photomultiplier receiver. The photomultiplier assembly may further include power circuitry.

In yet further examples, the pressed insert is about one millimeter to about ten millimeters in thickness. The assembly may further include an elongated test sample holder. In other examples, the housing is stationary. For instance, the luminometer may be a bench-top laboratory device.

Still another embodiment of the present disclosure is a luminometer for use with a test sample holder to determine the emitted light from the test sample holder. The luminometer may comprise a housing, a photomultiplier assembly and a chamber. Typically, the housing includes a sample port and an entrance tube that is generally aligned with the sample port and is generally adapted to accept the test sample holder into the housing. The photomultiplier assembly typically has at least one photomultiplier tube. Further, the chamber is typically positioned between the entrance tube and the photomultiplier tube. The chamber may include an insert chosen from a polytetrafluoroethylene (PTFE) pressed insert or a mirrored surface, at least one photomultiplier tube and a pressed deactivator. In some examples, the pressed insert may have a thickness of about two millimeters to about four millimeters and is substantially floating within the chamber and having a first tube opening to receive the entrance tube and a second deactivator opening. The photomultiplier assembly may have at least one photomultiplier tube. The pressed deactivator has a thickness of about two millimeters to about four millimeters secured in the second deactivator opening.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which.

DESCRIPTION OF EMBODIMENTS

Figure 1:
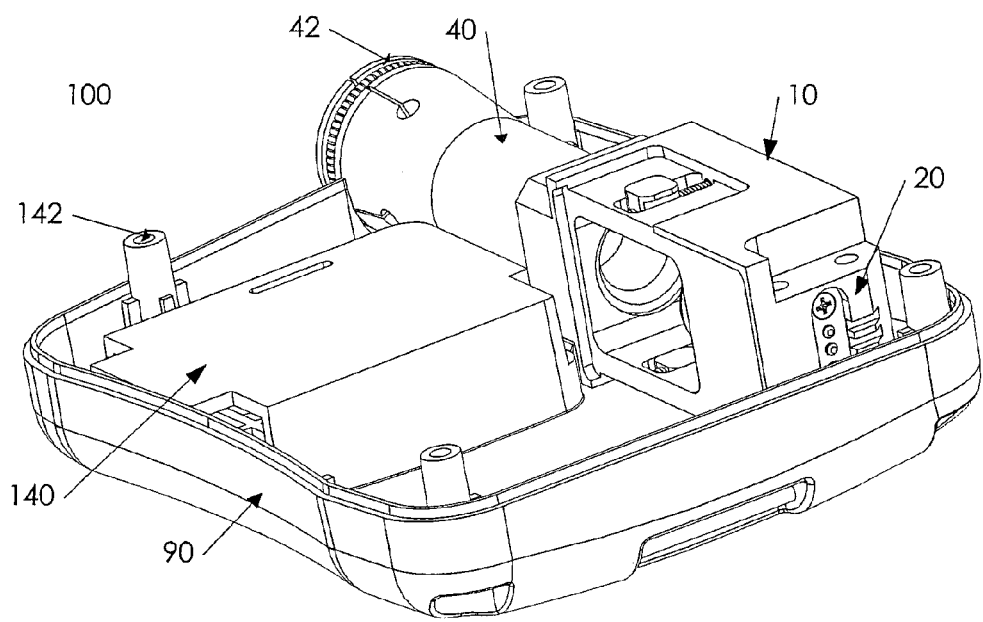
FIG. 1 is a side perspective view of a luminometer according to an embodiment of the disclosure, with elements removed to show internal components.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Referring now to the drawings in general and FIG. 1 in particular, it will be understood that the illustrations are for the purpose of describing embodiments of the disclosure and are not intended to limit the disclosure or any invention thereto. As best seen in FIG. 1, a luminometer 100 is shown embodied according to the present disclosure. A luminometer 100 may include a housing and shutter for sealing a test sample in the luminometer 100 for the determination of emitted light from the test sample. The luminometer 100 includes an improved chamber 10 having a pressed polytetrafluoroethylene insert (not shown in FIG. 1) for improved efficiency and minimized photon loss during testing. Embodiments of the luminometer 100 may be handheld portable devices and stationary laboratory bench units as interchangeably described herein. Further embodiments of the luminometer 100 work in conjunction with a variety of sample holders described herein to determine and measure the presence of ATP, pesticides, phosphatase, somatic cells, as well has a wide range of analytical tests for the quality of a wide variety of products.

FIG. 1 shows certain elements of the bottom section of one embodiment of a hand-held luminometer 100. Additional embodiments include a variety of designs and arrangements of other hand-held luminometers, as well as non-hand held stationary luminometers, while including any of improved internal components described herein to increase the efficiency of capturing light readings by measuring photo output using photomultiplier tubes, photodiodes and the like. Typically, the hand-held luminometer 100 has an outer case, including a case having a bottom casing 90 as illustrated in FIG. 1 to help protect the internal components. The bottom casing 90 generally has an opening to receive the sample port 42 and entrance tube 40. In particular examples, the opening in the bottom casing 90 includes a seal, for sealing environmental elements out of the luminometer 100. As shown in FIG. 1, a plurality of securing members 142 on the bottom casing 90 may mate with corresponding securing members on the opposing upper casing. Luminomoter elements useful for detecting and measuring luminescence in test materials are disclosed, for example, in U.S. Pat. No. 4,213,703, issued Jul. 22, 1980, U.S. Design Pat. No. D393,601, issued Apr. 21, 1998; U.S. Pat. No. 5,917,592, issued Jun. 29, 1999; and U.S. Pat. No. 6,055,050, issued Apr. 25, 2000, all of which are incorporated herein by reference in their entireties.

FIG. 1 further shows the chamber 10 aligned between the entrance tube 40 and the photomultiplier assembly 20 in an optical path from the chamber 10 to a photosensitive device of the photomultiplier assembly 20 to receive emitted light from a test sample. Therefore, the mounting of the chamber 10 is generally in relationship to the photomultiplier assembly 20 for the detection of the light transmitted from the sample chamber 10. The end of the chamber 10 opposing the photomultiplier assembly 20 may include a chamber block 32 to generally secure the distal end of the entrance tube 40.

Figure 2:
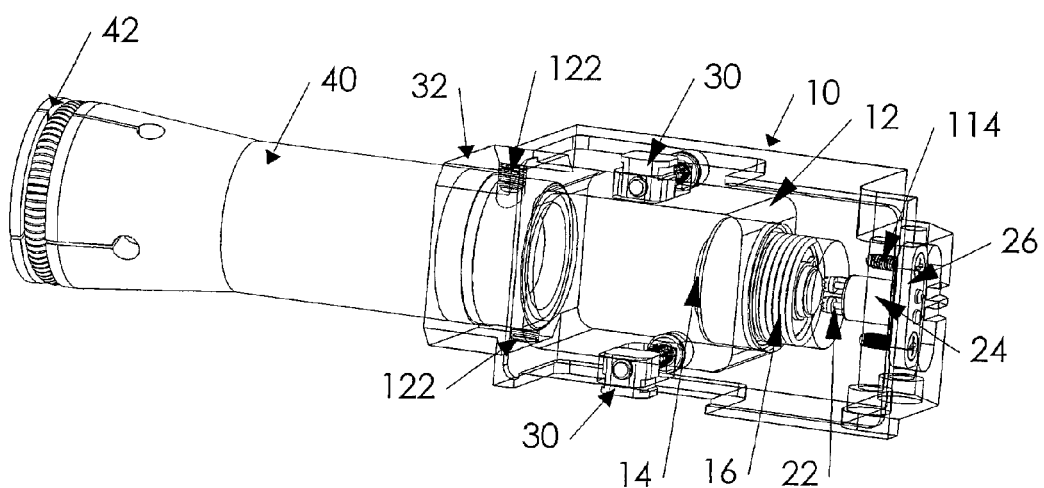
FIG. 2 is a side perspective view of chamber and entrance tube elements introduced in the embodiment of FIG. 1, with elements removed for clarity.

FIG. 2 shows certain internal components of one embodiment of the assembled chamber 10. Typically, the proximate end of the entrance tube 40 includes a sample port 42 to generally receive any of the test sample holder embodiments described or incorporated herein. As shown, the distal end of the entrance tube 40 may be positioned in the chamber block 32 and secured thereto with at least one fastener 122. In this particular example, a pair of opposing fasteners 122 secure the entrance tube and the chamber block 32. Additional embodiments include other positioning and fastening arrangements, including other structural and/or adhesive configurations.

Typically, the chamber 10 supports an internal insert 12 between the entrance tube 40 and the photomultiplier assembly. As shown in FIG. 2, a pair of opposing braces 30 may support the insert 12 within the chamber 10. For instance, the braces 30 may float the insert 12 within the interior of the chamber 10. The braces 30 may be adjustable to properly align the insert 12 within the chamber 10. The insert 12 typically includes openings on opposing ends as discussed hereinafter. In particular examples, the insert 12 is comprised of highly reflective synthetic material, for instance, mirrored surfaces, a pressed polytetrafluoroethylene (PTFE), a smoked magnesium oxide, a pressed magnesium oxide powder, a pressed barium sulfate powder, or similar glasses, tiles, plastics and the like. Applicants have discovered unexpected results from reflective chambers 10, including mirrored inner side faces, as shown and described herein. Other examples of the insert 12 include a variety of other reflective materials and arrangements.

As further shown in FIG. 2, a deactivator 14 is typically positioned in an opposing opening in the insert 12, i.e. opposite the entrance chute opening. The deactivator 14 may protrude through the diverter opening of the insert 12 and extend rearward beyond the insert 12. In particular examples, the deactivator 14 is comprised of a highly reflective synthetic material, for instance a pressed polytetrafluoroethylene (PTFE), a mirrored surface, a smoked magnesium oxide, a pressed magnesium oxide powder, a pressed barium sulfate powder, or similar glasses, tiles, plastics and the like. Typically, the PTFE is a white solid at room temperature. Other examples of the deactivator 14 include a variety of other reflective materials and arrangements.

The chamber 10 may additionally support the photomultiplier assembly. For instance, as shown in FIG. 2, the rear end of the chamber may support a receptor panel 26 secured thereto with fasteners 114. The receptor panel 26 may support a photomultiplier receiver 24 and may have electrical connections to the electrical power circuitry, which generally support at least one photomultiplier tube 22. FIG. 2 shows one particular example with two photomultiplier tubes 22. Other examples include a plurality of photomultiplier tube 22 configurations.

Figure 3:
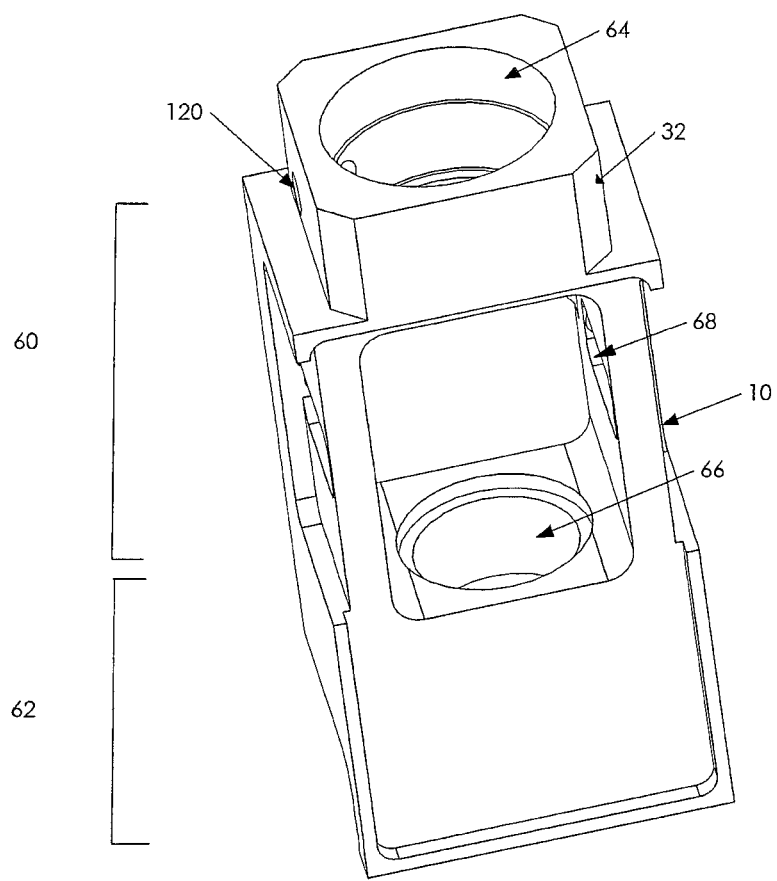
FIG. 3 is an isolated side perspective view of a chamber according to the embodiment of FIG. 1.

FIG. 3 shows one embodiment of a chamber 10 with elements removed to illustrate the chamber block 32, insert portion 60 and the photomultiplier portion 62. As shown, the chamber block 32 is positioned on the front side of the chamber and generally includes a tube cavity 64 that is adapted to receive the entrance tube (not shown). At least one fastener hole 120 in the chamber block 32 may secure the chamber 10 in position with other internal components of the luminometer 100.

The insert portion 60 of the chamber may be sized to receive and retain any of inserts shown and described herein. The opposing faces of the insert portion 60 may further include brace supports 68 to help adjust the alignment of the insert within the housing, for instance in the floating orientation described herein.

The photomultiplier portion 62 may include a deactivator cavity 66 to receive any of the deactivators show or described herein. Further, the photomultiplier portion 62 may include any of the photomultiplier assembly components incorporated and shown/described herein.

Figure 4:
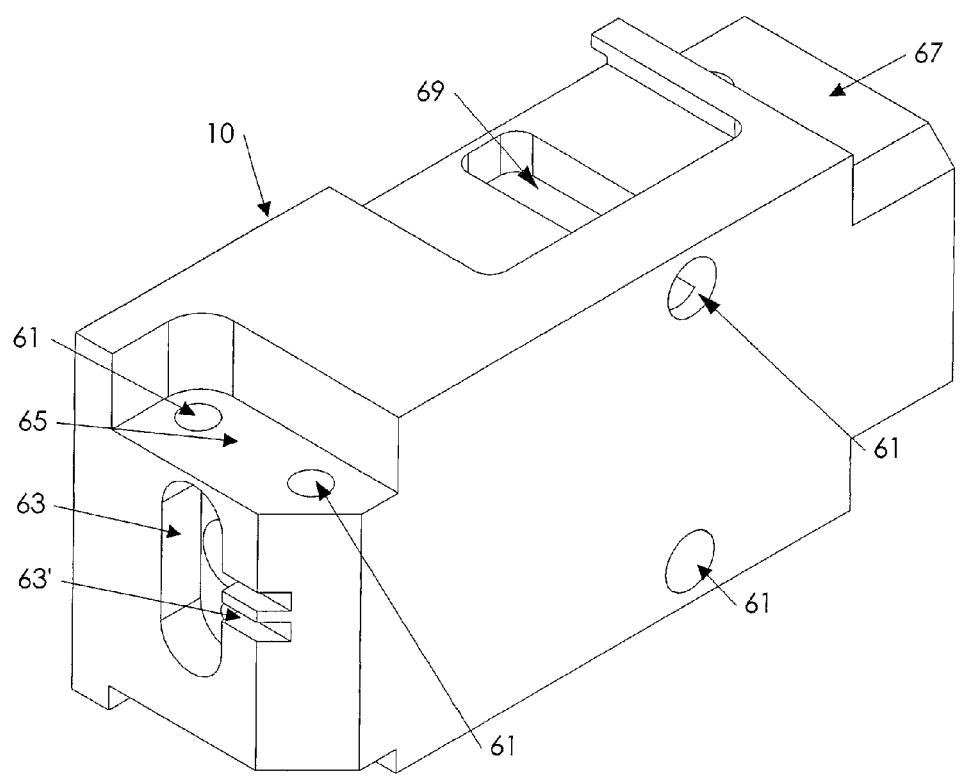
FIG. 4 is a rear perspective view of the chamber shown in FIG. 3.

FIG. 4 illustrates the rear view of one embodiment of chamber 10. In this embodiment, the rear of chamber 10 includes a receptor cavity 63 to allow electrical communication between the photomultiplier elements and the electronics outside of the chamber 10. As shown, the receptor cavity 63 may include slits 63' to allow for adjusting of the electronic components within the chamber 10. Further, the rear portion may include a rear assembly lip 65 to mate with corresponding components within the luminometer assembly and/or housing for a compact fitting. Fastener holes 61 may receive and retain fasteners to secure the chamber 10 to any of the internal luminometer components.

As also seen in FIG. 4, the side faces of the chamber 10 may include a plurality of fastener holes 61 to receive and retain fasteners to secure the chamber 10 to any of the internal luminometer components. In addition, the front portion may include a front assembly lip 67 to mate with corresponding components within the luminometer. Similarly, fastener holes may receive and retain fasteners and the like to secure the chamber to any of the internal luminometer components. As shown the top surface of the chamber 10 may include a top cavity 69 to allow access within the internal portions of the chamber.

Figure 5:
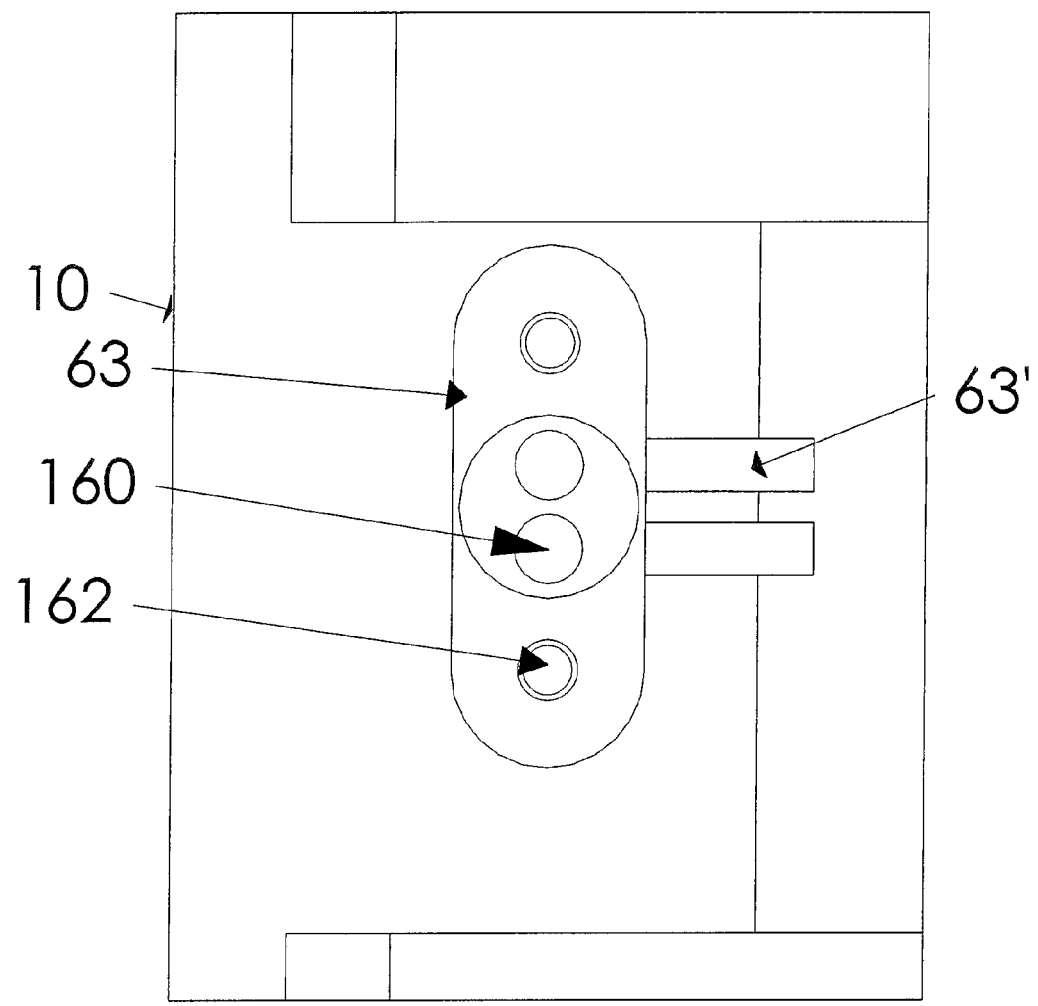
FIG. 5 is a rear view of the chamber shown in FIG. 3.

FIG. 5 better shows the rear face of one embodiment of the chamber 10. As illustrated, fastener holes 162 may receive and retain the receptor cavity 63. The receptor cavity 63 may include slits 63' to allow for adjusting of the electronic components within the chamber 10.

Figure 6:
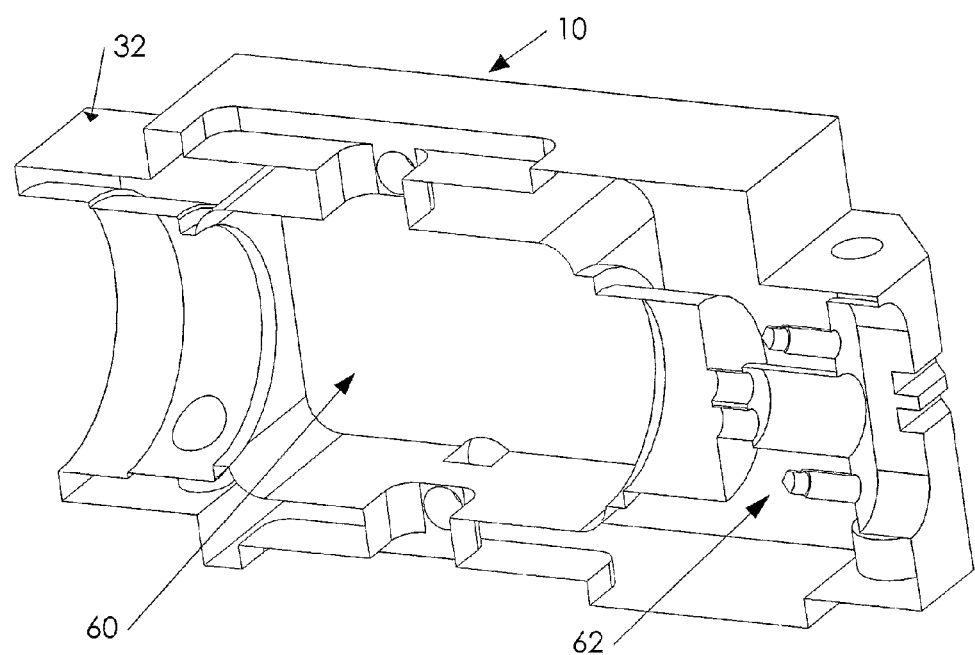
FIG. 6 is a cross-sectional side view of the chamber shown in FIG. 3.

FIG. 6 illustrates inner components of one example of a chamber 10, with the insert and other elements removed for clarity. The front of the chamber includes the chamber block 32. The central portion of the chamber 10 includes the insert portion 60. The rear portion of the chamber 10 includes the photomultiplier portion 62.

Figure 7:
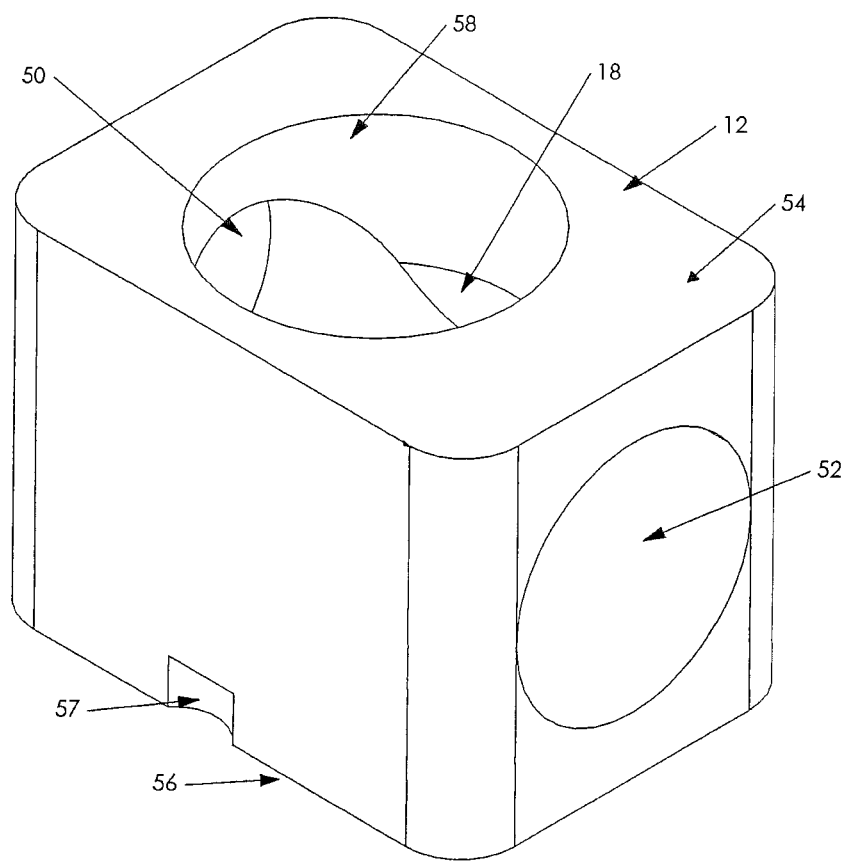
FIG. 7 is an isolated side perspective view of an insert according to the embodiment of FIG. 2.

FIG. 7 shows one embodiment of the insert 12. Typically, the insert 12 is comprised of a highly reflective synthetic material, for instance a pressed polytetrafluoroethylene (PTFE), a mirrored surface, a smoked magnesium oxide, a pressed magnesium oxide powder, a pressed barium sulfate powder, or similar glasses, tiles, plastics and the like. In these examples the solid white PTFE piece insert exhibits superior optical performance when the thickness is in the range of about one millimeter to about ten millimeters, and in the range of about two millimeters to about four millimeters in particular. Applicant has discovered that in particular examples, the optical performance did not increase but stayed the same when the thickness was greater than about five millimeters. The top wall 54 generally includes a top opening 58. The front face of the insert 10 includes a first tube opening 50. The opposing rear face of the insert 10 may include a second deactivator opening 52. The bottom wall 56 may include attachment points 57 to attach to any of the brace configurations herein for a substantially floating insert arrangement. However, those of ordinary skill in the art having the benefit of this disclosure will recognize other examples include a variety of opening, brace and orientation configurations.

Figure 8:
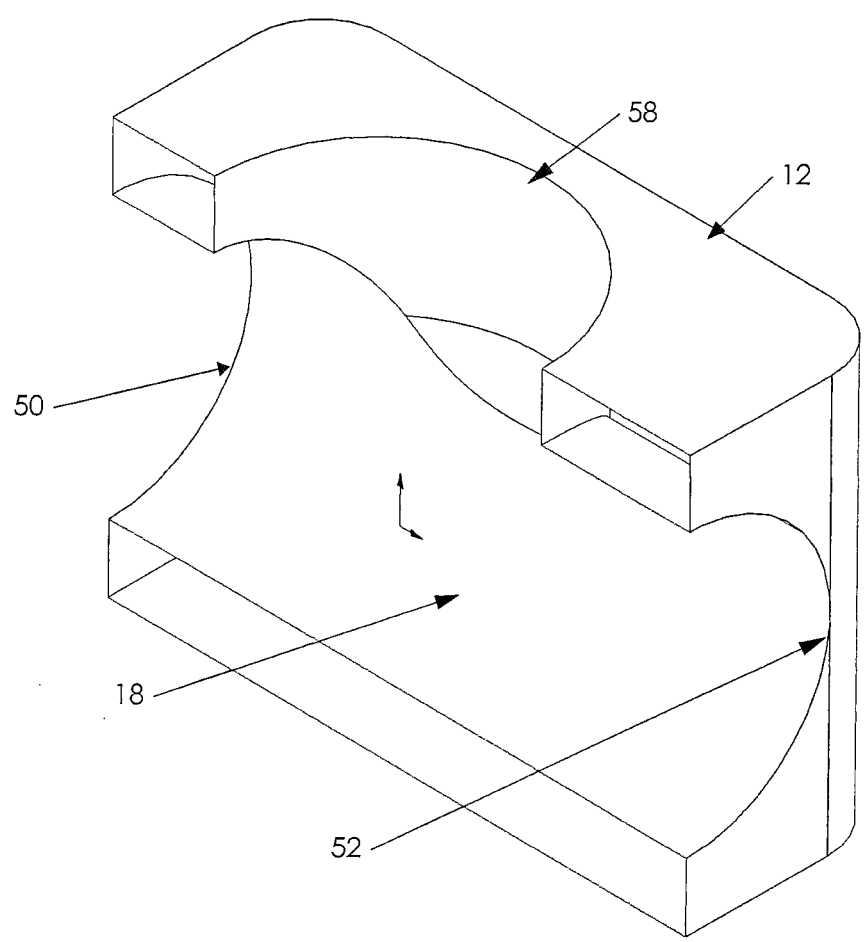
FIG. 8 is a cross-sectional side view of the insert shown in FIG. 7.

FIG. 8 illustrates inner components of one example of an insert 10 with particular elements removed for clarity. The front of the insert 10 may include the first tube opening 50. The insert may include a mirrored surface, a smoked magnesium oxide, a pressed magnesium oxide powder, a pressed barium sulfate powder, or similar glasses, tiles, plastics and the like. Further, the opposing rear face of the insert 10 may include a second deactivator opening 52.

Figure 9:
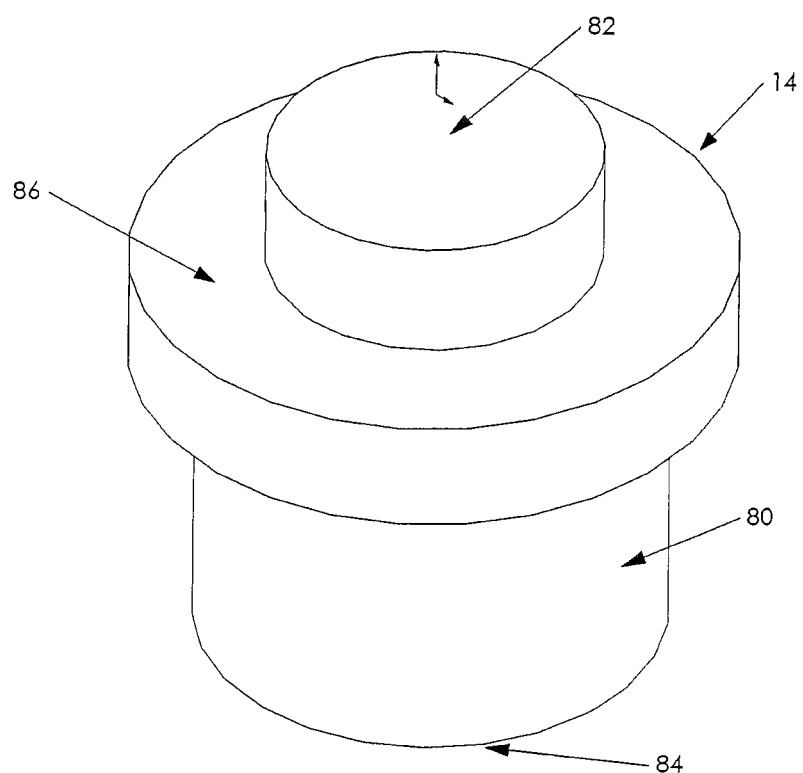
FIG. 9 is an isolated side perspective view of a deactivator according to the embodiment of FIG. 2.

FIG. 9 shows one example of the deactivator 14 that is typically positioned within the deactivator opening in the insert 12 as discussed herein. Typically, the deactivator 14 is comprised of a highly reflective synthetic material, for instance a pressed polytetrafluoroethylene (PTFE), a smoked magnesium oxide, a pressed magnesium oxide powder, a pressed barium sulfate powder, or similar glasses, tiles, plastics and the like. In these examples the solid white PTFE piece deactivator exhibits superior optical performance when the thickness is in the range of about one millimeter to about five millimeter, and in the range of about two millimeters to about four millimeters in particular. As shown, the deactivator 14 includes a ledge 86 that fits snuggly to the insert 12 to increase efficiency, i.e. reduce photon loss. For instance, the body 80 below the ledge 86 generally fits snugly into the deactivator opening. Further, the upper surface of the deactivator 14 includes the insert aperture 82. Other embodiments include a variety of insert aperture sizes and configurations. The lower surface 84 of the deactivator 14 is generally aligned with the photomultiplier assembly, including the photomultiplier tubes, and may include a photomultiplier aperture.

Figure 10:
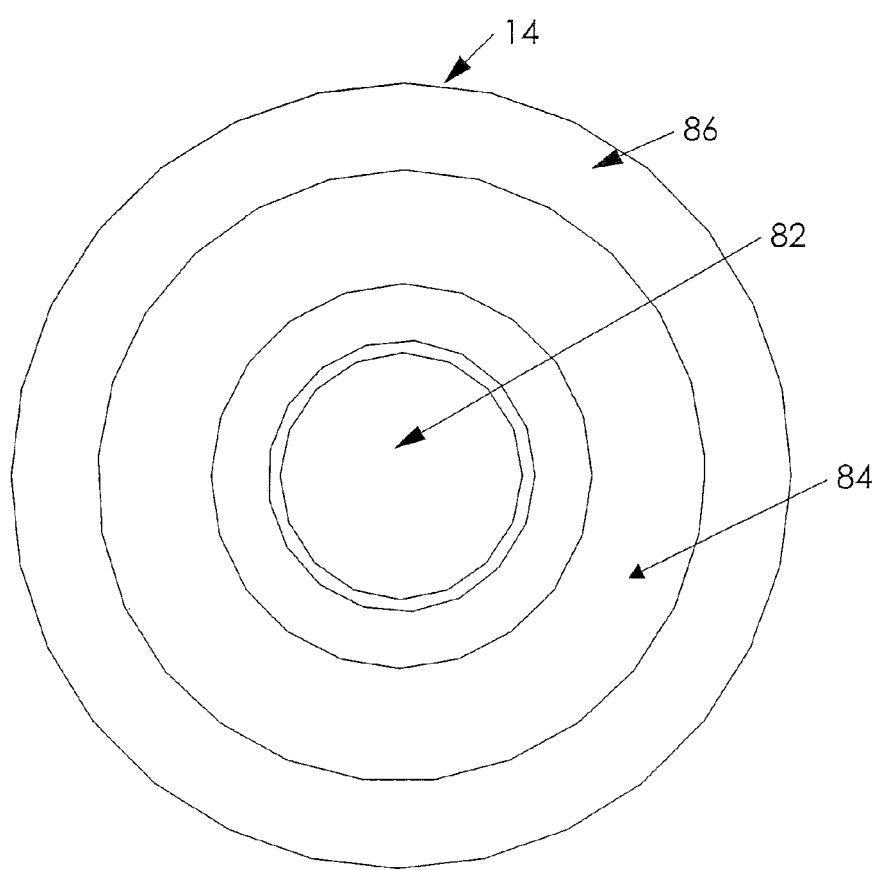
FIG. 10 is a bottom view of the deactivator shown in FIG. 9.
Figure 11:
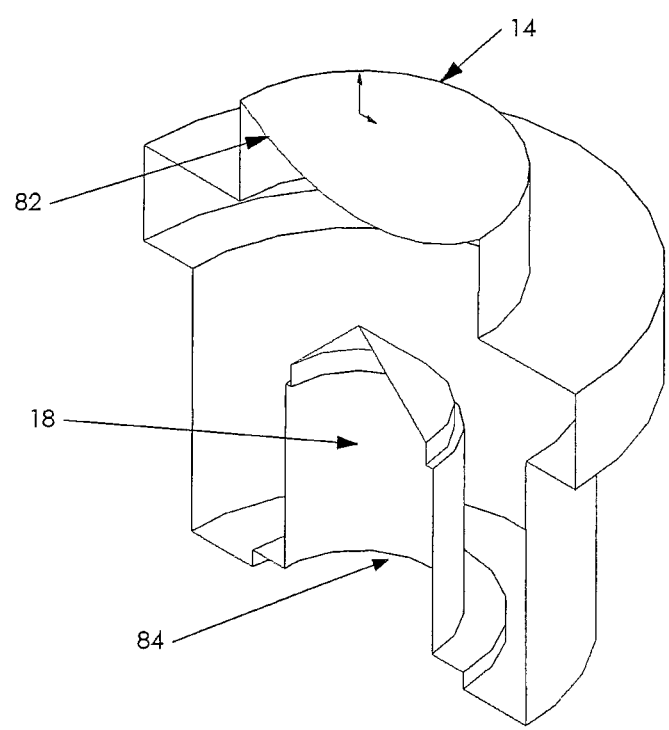
FIG. 11 cross-sectional side view of the deactivator shown in FIG. 9.

FIG. 10 illustrates a bottom view of one example of the deactivator 14. As shown, the insert aperture 82 extends throughout the deactivator 14. The lower surface 84 of the deactivator 14 is generally recessed from the ledge 86. FIG. 11 illustrates inner components of one example of a deactivator 14 with particular elements removed for clarity. The top surface of the deactivator 14 generally includes the insert aperture 82. In particular examples, the deactivator 14 may include a pressed polytetrafluoroethylene (PTFE), a mirrored surface, a smoked magnesium oxide, a pressed magnesium oxide powder, a pressed barium sulfate powder, or similar glasses, tiles, plastics and the like. Further, the opposing bottom face of the deactivator 14 may include a lower surface 84 that is generally aligned with any of the photomultiplier assembly components shown and described herein.

Figure 12:
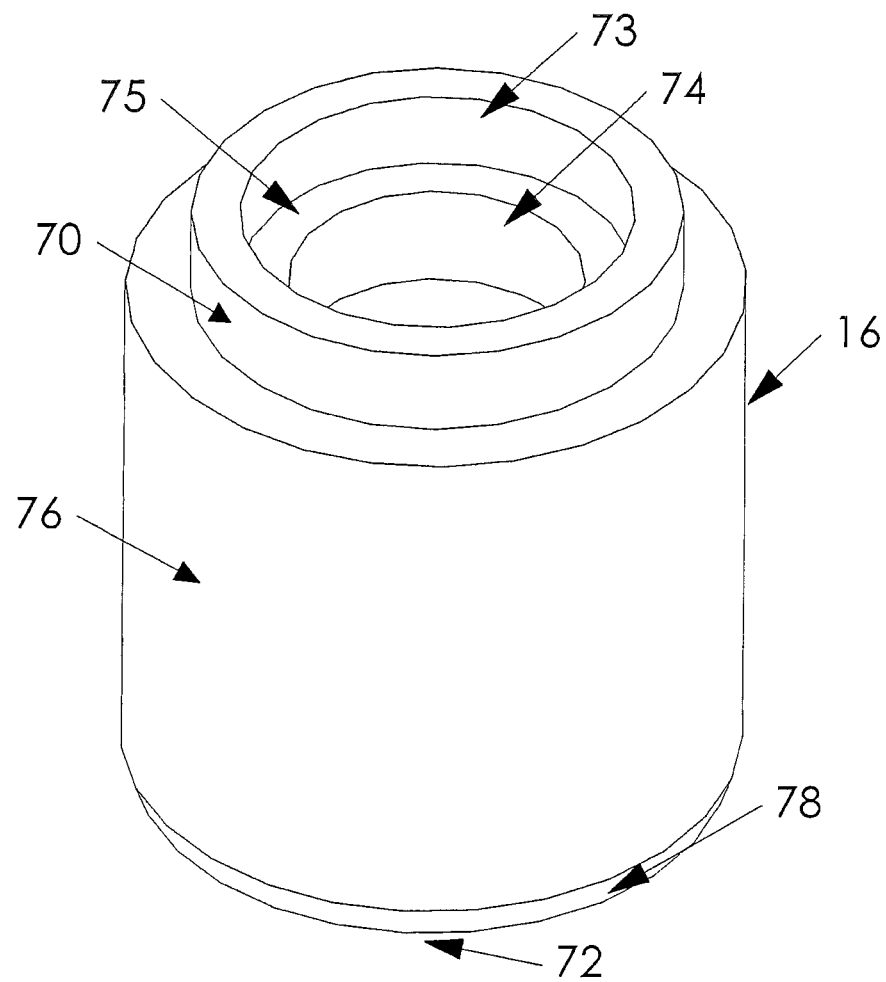
FIG. 12 is an isolated side perspective view of a shutter according to the embodiment of FIG. 2.

FIG. 12 illustrates one example of the shutter 16 for generally sealing any of the test samples descried herein to prevent the interference of external light when the device is in operation. Typically, the shutter 16 is composed of a black thermoplastic material, for instance a black DELRIN material produced by DuPont or the like. In particular examples, the shutter 16 includes high stiffness and dimensional stability to overlay with the PTFE pressed materials described herein for optimized performance. The shutter 16 is sized down to align with the optimum thickness of the pressed PTFE materials to provided improved optical performance. As shown in FIG. 12, the upper surface of the shutter 16 includes the first shutter opening 74. In some examples, the shutter opening 74 includes a series of narrowing rims 73, 70 into the body 76 of the shutter 16. The inner portion of the narrowing rim section may include a recessed ledge 75. As illustrated in FIG. 12, the lower portion of the body 76 may include a tapered edge 78 leading to the second first shutter opening 72, i.e. the shutter opening opposing the first shutter opening.

Figure 13:
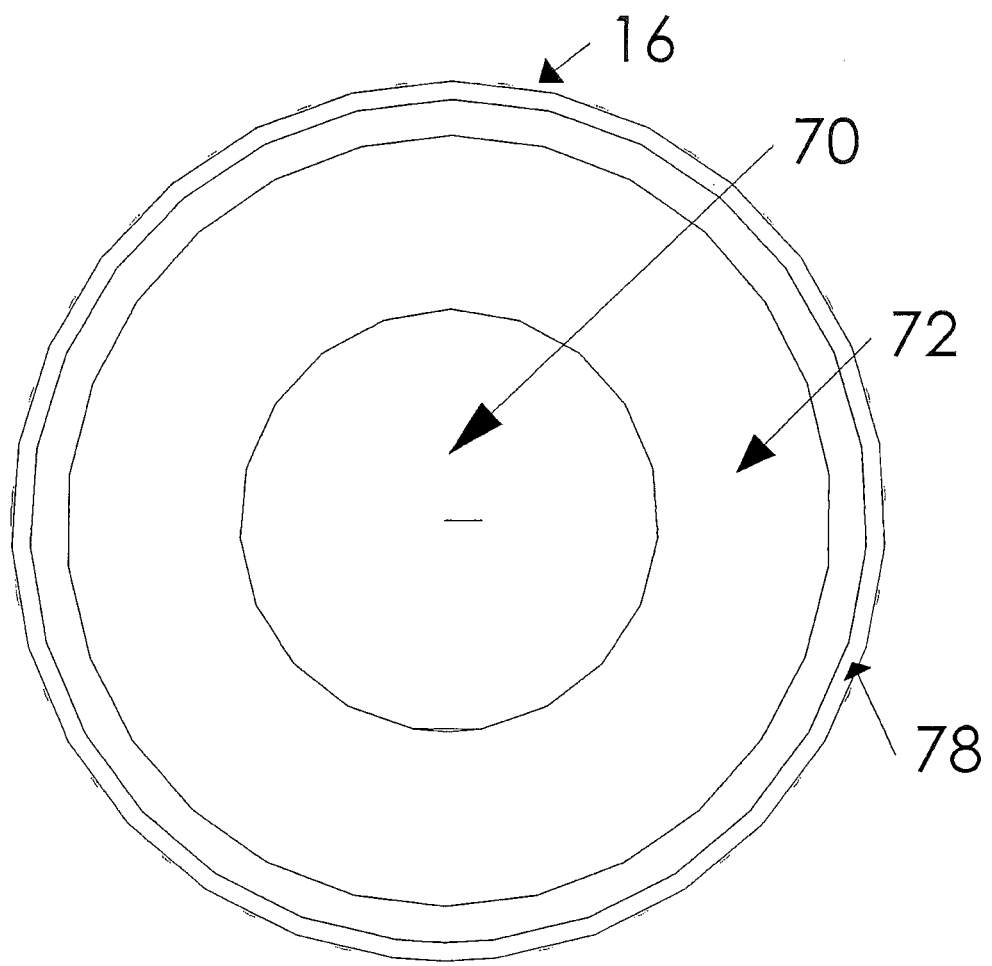
FIG. 13 is a bottom view of the shutter shown in FIG. 12.
Figure 14:
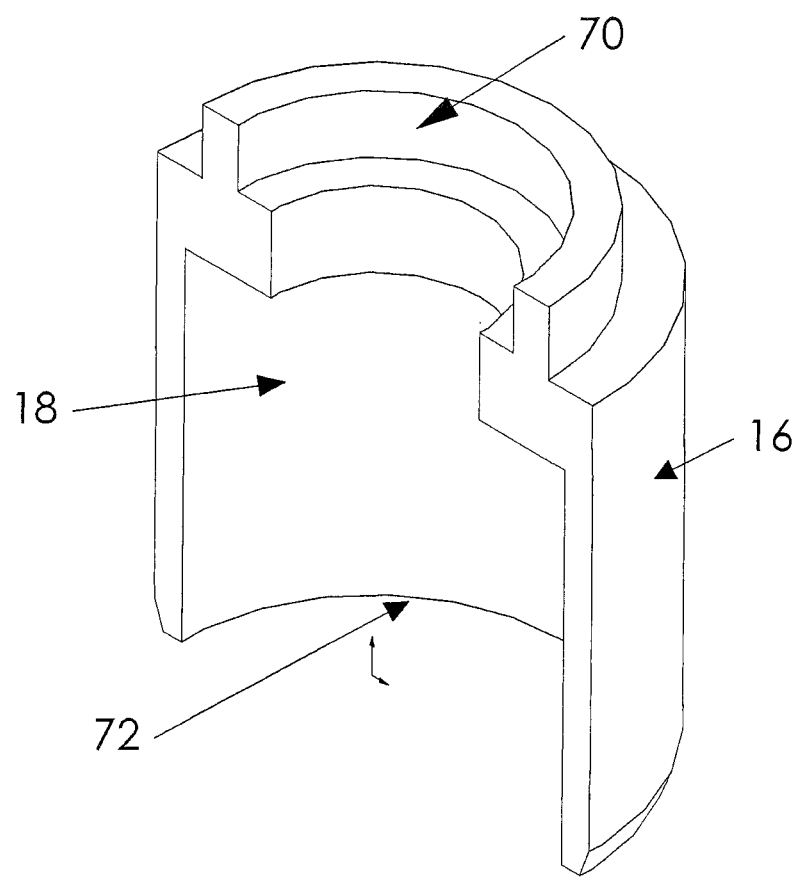
FIG. 14 cross-sectional side view of the shutter shown in FIG. 12.

FIG. 13 illustrates a bottom view of one example of the shutter 16 comprising a generally opaque composition to shield the photosensitive device from light transmitted from the sample chamber 10. As shown, the first shutter opening 74 extends throughout the shutter 16 for the communication between the photosensitive assembly, which may be a photomultiplier tube, and the light path from the sample chamber 10, for instance when the shutter is in an open position. The second first shutter opening 72 of the shutter 16 is generally recessed from the tapered edge 78. FIG. 14 illustrates inner components of one example of member 16 with particular elements removed for clarity.

Figure 15:
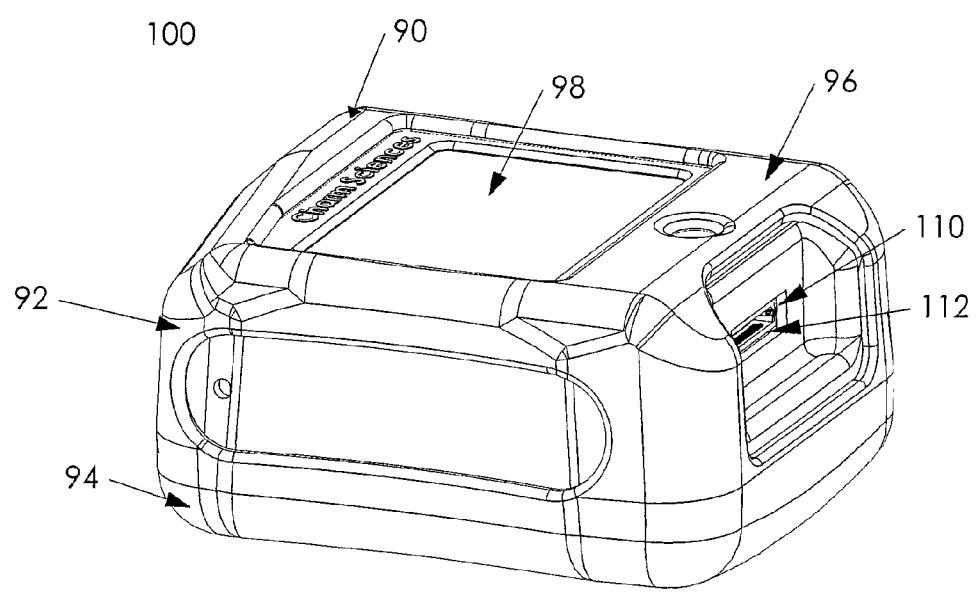
FIG. 15 is a side perspective view of a luminometer according to one embodiment of the disclosure.

FIG. 15 illustrates one embodiment of the luminometer 100 which includes any of the internal components described herein. For instance, the luminometer 100 includes a split case assembly having a top case 92 and a bottom case 94 that are removably secured to one another. In particular examples the top case 92 and the bottom case 94 are generally sealed together in the closed position to protect internal components from dirt, debris and improper readings. In some examples, portions of the outer periphery of the luminometer 100 is protected with a bumper 90, for instance acting as a protective layer.

As shown in the FIG. 15, the front face of this example of the luminometer 100 includes a touch screen display 98, whereby the operator may operate the device through touch screen manipulations. In particular examples, the display 98 is a high resolution display. For instance, display 98 may be backlight, sunlight-readable alphanumeric display. The luminometer 100 may further include touch-screen controls and/or a toggle feature and keypad. The keypad may be water-resistant and durable. In addition, the bottom portion of this example of the luminometer 100 includes access to a PCB assembly 110 having a PCT board 112. Those of ordinary skill in the art having this disclosure will recognize that the PCB assembly and related components may be positioned in a variety of locations on the luminometer 100 and comprise a variety of electrical arrangements to match the particular application.

Figure 16:
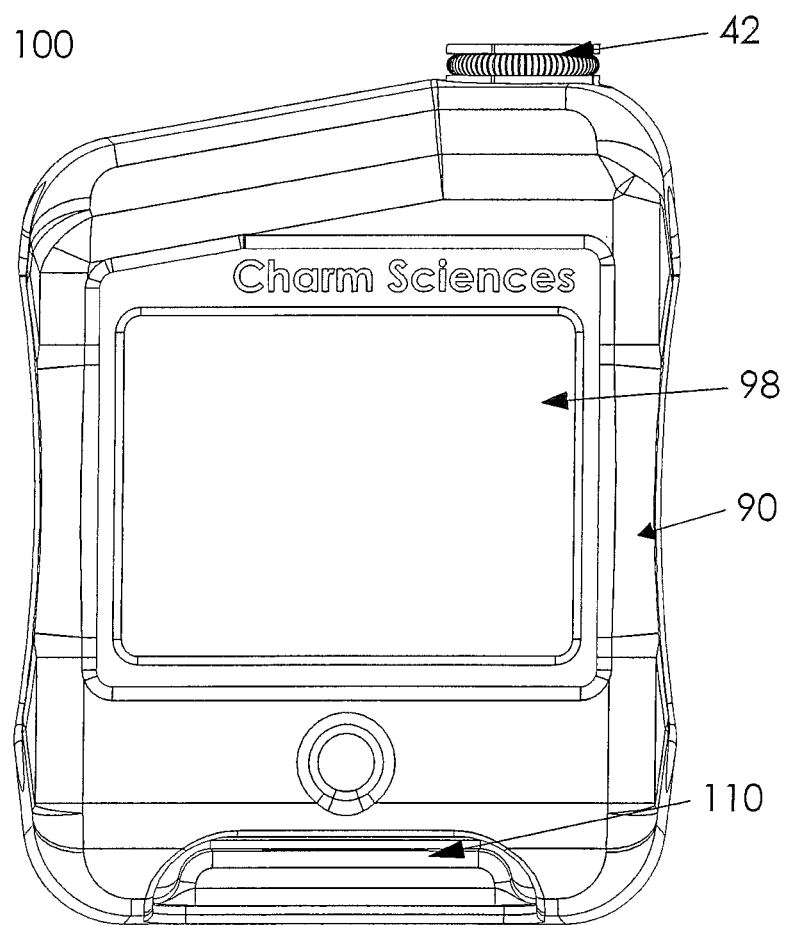
FIG. 16 is a front view of the luminometer shown in FIG. 15.

FIG. 16 illustrates one ergonomic design of the luminometer 100. As shown, the luminometer 100 design is wider than high which allows easy two-handed gripping, with two thumb control on the touch screen display 98. In yet further examples, the luminometer 100 is for single-hand held operation.

In yet other embodiments, any of the stationary and/or portable luminometers described herein may include an outlet for a power supply, other than a battery pack, a communication jack, i.e. a phone jack and the like.

In use, a light blocking portable test sample holder is inserted into the entrance port 42. The test sample holder may have a tubular body with a light-blocking upper portion and a lower, clear vial section. For instance, the holder may have a light-blocking upper cap, a light blocking intermediate tubular body section, and a lower, clear test sample vial section. The upper cap may have a vertically-extending raised line thereon and internal threads on the lower surface. The intermediate light-blocking tube may have an upper and lower section, divided by a raised horizontal peripheral ridge. The upper section of tube may have threads with an indicator arrow and a vertical, indented, flat marking area thereon. The lower section of tube may be smooth and rounded, with a bottom section of slightly reduced diameter. In yet other particular examples, the translucent test sample vial, with test sample therein, may be detachably secured onto the lower section of the intermediate tube by a threaded top section, which threads into an inner threaded portion on the lower section. Further, the vertical grip ridges may provide for ease in threadably securing the test sample vial, and horizontal ridge on the test vial provides for a stopping means for the threaded section.

In particular examples, useful portable test sample holder elements and related luminimoter elements useful for the detection of sample analytes are described U.S. Design Pat. No. D388,519, issued Dec. 30, 1997; U.S. Pat. No. 5,827,675, issued Oct. 27, 1998; U.S. Pat. No. 5,965,453, issued Oct. 12, 1999; U.S. Pat. No. 5,985,675, issued Nov. 16, 1999; U.S. Pat. No. 7,229,783, issued Jun. 12, 2007; and U.S. Pat. No. 7,993,871, issued Aug. 9, 2011, all of which are incorporated herein by reference in their entireties.

In other embodiments, the disclosure includes a luminometer kit. In this embodiment, the kit may comprise a luminometer e.g. any of the luminometer elements previously shown or described. Further, the kit may comprise a chamber e.g. any of the chamber and/or insert elements previously shown or described.

The following examples demonstrate the efficacy and utility of the present inventions.

EXAMPLES

Optics Simulation 1

The optics of the luminometer chamber shown and described herein were examined to characterize the improved light collection. During simulations, the inner face of the chamber and the inner face of the window were altered from absorption material, reflective material, and diffusion material. The following chart illustrates various simulations of the inner chamber and window face arrangements.

As shown in the charts, the simulations note significant improvement with the reflected chamber and absorbing window. For instance, the mirrored inner side face provided unexpected specular reflection results as generally shown and described herein. Further, the absorbing window, i.e. a black painted window inner side face, provided unexpected diffuse reflection results as shown and described herein.

| Inner Chamber Face | Window Face | Total Irradiance Power (%) | Improvement Ratio (%) |
|---|---|---|---|
| Mirror (95%) | Absorbing | 6.71 | 100.0 |
| Mirror (95%) | Flat White Finish (90%) | 9.43 | 140.5 |
| Mirror (95%) | Mirror (95%) | 12.78 | 190.5 |
| Flat White Finish (90%) | Absorbing | 8.71 | 129.8 |
| Flat White Finish (90%) | Flat White Finish (90%) | 12.12 | 180.6 |
| Flat White Finish (90%) | Mirror (95%) | 15.61 | 232.6 |
| Mirror (95%) | Absorbing | 2.61 | 38.9 |
| Mirror (95%) | Flat White Finish (90%) | 3.52 | 52.5 |
| Mirror (95%) | Mirror (95%) | 4.36 | 65.0 |
| Flat White Finish (90%) | Absorbing | 3.59 | 53.5 |
| Flat White Finish (90%) | Flat White Finish (90%) | 4.71 | 70.2 |
| Flat White Finish (90%) | Mirror (95%) | 5.42 | 80.8 |
| Absorbing | Absorbing | 0.60 | 9.0 |

-continued

| Inner Chamber Face | Window Face | Total Irradiance Power (%) | Improvement Ratio (%) |
|---|---|---|---|
| Mirror (95%) | Mirror (95%) | 0.72 | 10.8 |
| Flat White Finish (90%) | Flat White Finish (90%) | 0.89 | 13.4 |

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular forms "a," "an," and "the" include plural referents unless expressly and unequivocally limited to one referent.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein, and every number between the end points. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10, as well as all ranges beginning and ending within the end points, e.g. 2 to 9, 3 to 8, 3 to 9, 4 to 7, and finally to each number 1, 2, 3, 4, 5, 6, 7, 8, 9 and 10 contained within the range.

We claim:

1. A luminometer for use with a test sample holder, said luminometer comprising:
    a. a housing having a sample port and an entrance tube aligned with said sample port and adapted to accept said test sample holder into said housing;
    b. a photomultiplier assembly within said housing, said photomultiplier assembly having at least one photomultiplier tube; and
    c. a chamber positioned between said entrance tube and in an optical path with said photomultiplier tube and having a mirrored inner side face.

2. The luminometer of claim 1, wherein said entrance tube is light blocking.

3. The luminometer of claim 1, wherein said photomultiplier assembly includes a receptor panel.

4. The luminometer of claim 1, wherein said chamber's mirrored inner side face is adapted to provide about ninety five percent mirrored reflection.

5. The luminometer of claim 1, further including an absorbing window inner side face.

6. The luminometer of claim 5, wherein said absorbing window inner side face includes a layer of black paint.

7. In a luminometer having a housing with an entrance to accept a test sample, a chamber comprising:
    a. an insert portion having a mirrored inner face and being positioned within a cavity with a first opening aligned with said entrance and a second deactivator opening;
    b. a photomultiplier portion having at least one photomultiplier tube; and
    c. a deactivator secured in said second deactivator opening.

8. The chamber of claim 7, wherein said chamber includes an upper chamber attachment block.

9. The chamber of claim 8, wherein said chamber block includes a tube cavity adapted to receive an entrance tube.

10. The chamber of claim 8, wherein said chamber block includes a front assembly lip adapted to align with said housing.

11. The chamber of claim 7, wherein said insert includes a front tube opening.

12. The chamber of claim 7, wherein said insert includes a rear deactivator opening.

13. The chamber of claim 7, wherein said insert includes a top opening.

14. The chamber of claim 7, wherein said insert portion includes a deactivator cavity to receive said pressed deactivator.

15. The chamber of claim 7, wherein said insert portion includes a brace support.

16. The chamber of claim 7, wherein said photomultiplier portion includes a receptor cavity adapted to receive a photomultiplier receptor.

17. The chamber of claim 16, including a photomultiplier receptor.

18. A luminometer for use with a test sample holder to determine said emitted light from said test sample holder, said luminometer comprising:
    a. a housing having a sample port and an entrance tube aligned with said sample port and adapted to accept said test sample holder into said housing;
    b. a photomultiplier assembly having at least one photomultiplier tube; and
    c. a chamber positioned between said entrance tube and said photomultiplier tube and having:
        i. a mirrored inner side face and a first tube opening to receive said entrance tube and a second deactivator opening,
        ii. at least one photomultiplier tube, and
        iii. a deactivator secured in said second deactivator opening.

19. The device of claim 18, including an absorbing window inner side face.

20. The device of claim 19, wherein said absorbing window inner side face includes a layer of black paint.

* * * * *